(12) United States Patent
Konstorum et al.

(10) Patent No.: US 10,314,601 B2
(45) Date of Patent: Jun. 11, 2019

(54) SURGICAL TOOL FOR REMOVING KIDNEY STONE

(71) Applicant: Gyrus ACMI Inc., Southborough, MA (US)

(72) Inventors: Gregory S. Konstorum, Stamford, CT (US); Derek A. Affonce, Usbridge, MA (US); Judy L. Walish, West Roxbury, MA (US); Michael Perriello, Hopedale, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 348 days.

(21) Appl. No.: 14/884,477

(22) Filed: Oct. 15, 2015

(65) Prior Publication Data

US 2016/0166267 A1 Jun. 16, 2016

Related U.S. Application Data

(60) Provisional application No. 62/064,208, filed on Oct. 15, 2014.

(51) Int. Cl.
*A61B 17/221* (2006.01)

(52) U.S. Cl.
CPC .... *A61B 17/221* (2013.01); *A61B 2017/2212* (2013.01); *A61B 2217/005* (2013.01); *A61B 2217/007* (2013.01)

(58) Field of Classification Search
CPC ... A61B 17/221; A61B 2017/2212–2017/2217
See application file for complete search history.

(56) References Cited

U.S. PATENT DOCUMENTS

| 5,496,347 | A | 3/1996 | Hashoguchi et al. |
| 5,683,413 | A | 11/1997 | Miyagi |
| 6,210,398 | B1 | 4/2001 | Ouchi |
| 2013/0035695 | A1* | 2/2013 | Uihlein ............... A61B 17/221 606/127 |
| 2014/0257253 | A1* | 9/2014 | Jemison ........... A61B 17/32056 606/1 |

FOREIGN PATENT DOCUMENTS

| EP | 1561413 A1 | 8/2005 |
| EP | 2014238 A1 | 1/2009 |

* cited by examiner

*Primary Examiner* — Shaun David
(74) *Attorney, Agent, or Firm* — Harrington & Smith (57) ABSTRACT

A surgeon's tool for operating a basket device to capture and remove an object may include a controller including a piston and cylinder mechanism for selectively and securely controlling and operating a wire and a sheath of the basket device wherein the piston and the cylinder of the piston and cylinder mechanism may each be independently operated to separately actuate the basket device. The piston and cylinder controller mechanism may include a double piston and cylinder design including first and second biasing mechanisms for biasing the basket device toward a closed position and a latch mechanism for selectively securing the positions of the cylinders.

15 Claims, 11 Drawing Sheets

_Fig-4_

_Fig-5_

_Fig-6_

SURGICAL TOOL FOR REMOVING KIDNEY STONE

FIELD

The present disclosure generally relates to medical devices such as a surgical tool. More particularly, the present disclosure relates to a surgical tool for controlling the movement of a lumen, wire and basket for removing a foreign object, such as a kidney stone, from a human.

BACKGROUND

It is generally known to provide an extractor or lumen, wire and basket for removing a foreign object from a body. Surgical tools, including handles, are generally known for manipulating and controlling the lumen, wire and basket to capture and extract a foreign object using an endoscope. Various handle devices have been proposed including the use of shape memory alloys and highly complex mechanisms for more accurately controlling the wire and basket such as disclosed in U.S. Pat. No. 5,720,754, which discloses a medical device controller which uses a syringe-plunger mechanism insertable into a working channel of an endoscope and which may be used for controlling actuation of a kidney stone basket. U.S. Patent Application Publication No. 20130211415 discloses a means for manipulating a sheath and stone basket, and controlling a position of the sheath with respect to the stone basket within an endoscope. It is also generally known to use a syringe mechanism for delivering fluid to a bilumen catheter in a device which may include a basket and sheath such as disclosed in International Patent Application Publication No. WO2004069059A2.

Despite these known devices, there long remains a significant need for an improved surgical tool for controlling a basket device during a surgical procedure to remove an object from a body.

DETAILED DESCRIPTION

Referring in general to all of the Figures and in particular to FIGS. 1 through 8, an embodiment of a surgical tool, handle or controller 10 according to the present disclosure and teachings is provided for use in removing objects from a body, such as a kidney stone from the biliary or ureteral structures of an animal, including a human. The surgical tool 10 may include a piston and cylinder mechanism 20 as shown in FIGS. 3 through 8. The surgical tool 10 may also include a basket device 30 for insertion in a lumen of an endoscope (not shown).

Figure 8:
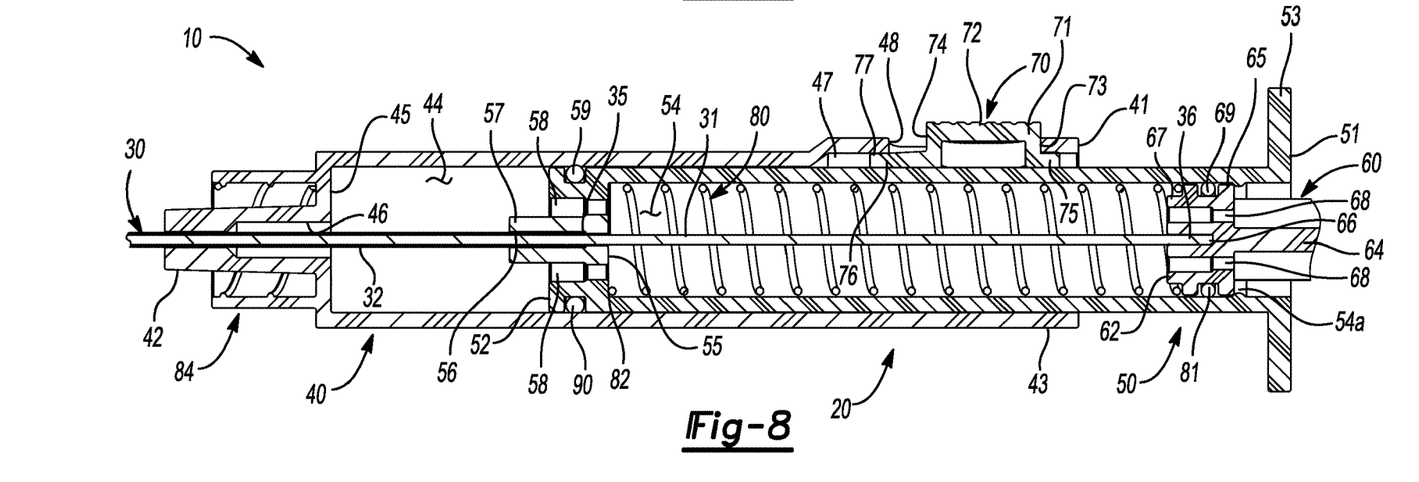
FIG. 8 is an alternate, partial, graphical side view of the surgical tool of FIG. 1.
Figures 17, 18:
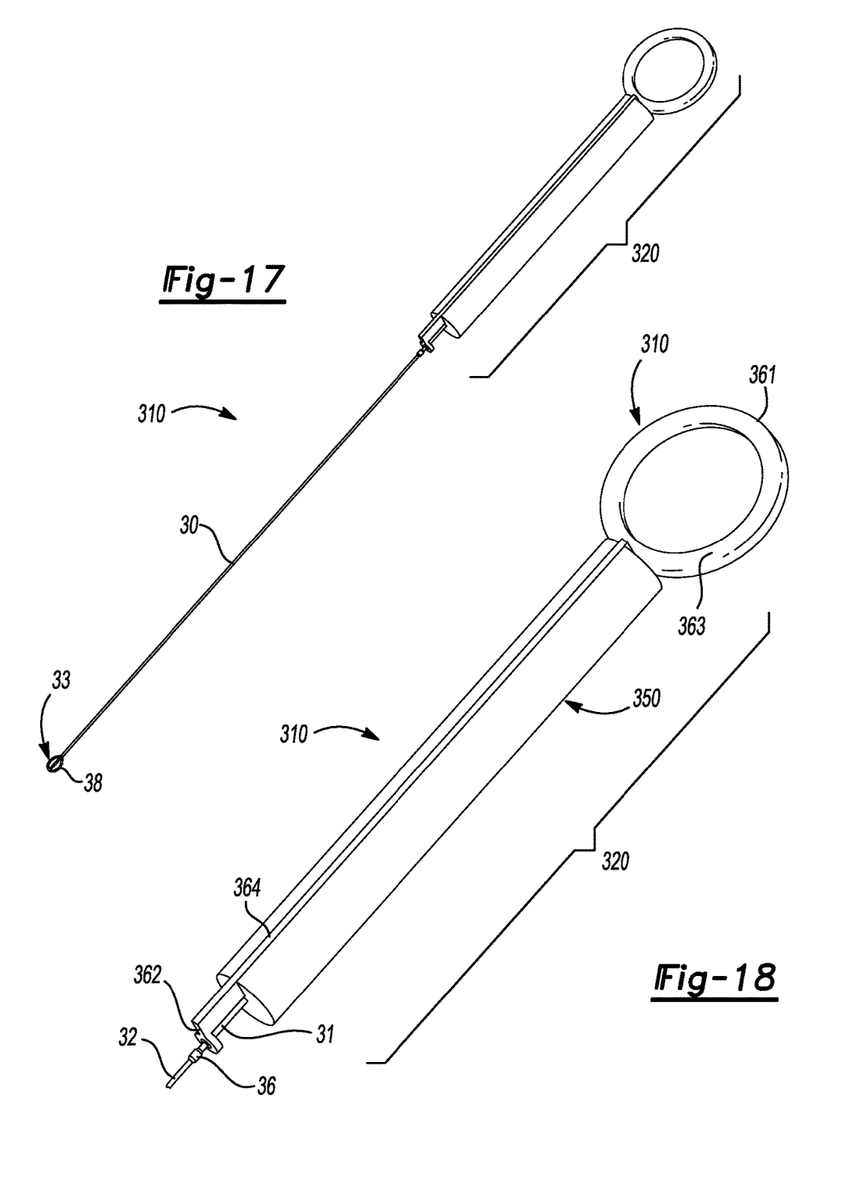
FIG. 17 is a graphic, perspective view of a surgical tool of one embodiment of the present disclosure.
FIG. 18 is an alternate, graphic, perspective view of the surgical tool of FIG. 17 in a first position.
Figure 21:
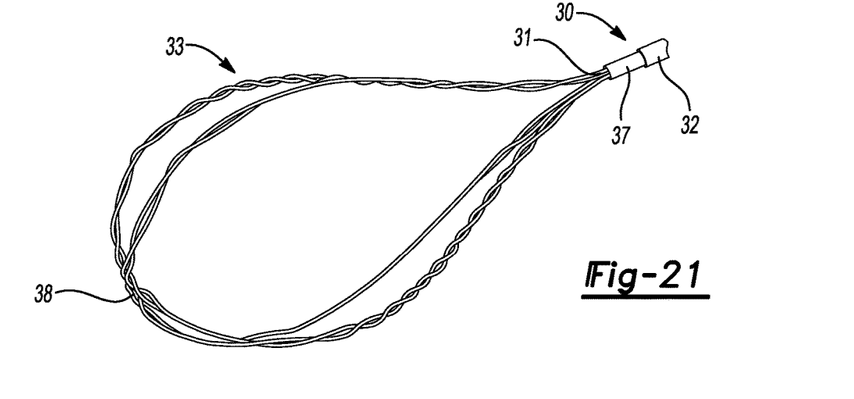
FIG. 21 is a partial, perspective graphic view of a wire basket of the present disclosure.

The basket device 30 may be of any generally known or appropriate type of construction and may generally include an outer sheath 32 and in inner wire assembly 31 capable of opening, forming a basket 33, and closing the basket 33 around a foreign object for removing the foreign object from a body. The sheath 32 of the basket wire device 30 may include a first or proximal end 35 which may be coupled to the inner or second housing 50, as shown in FIG. 8. The wire 31 of the basket device 30 may include a first or proximal end 36 which may be coupled to the plunger 60. The sheath 32 and the wire 31 may each include a second or distal end 37 and 38, respectively (as shown in FIGS. 17 and 21), opposite the first or proximal ends 35 and 36, respectively.

The piston and cylinder mechanism 20 of the surgical tool 10 may preferably include a first or outer housing 40 having a generally cylindrical shape, a second or inner housing 50 also having a generally cylindrical shape, and a plunger 60. The second or inner housing 50 is received in the first or outer housing 40 and the plunger 60 is received in the second or inner housing 50, as shown in FIGS. 1 through 3 and 7 through 8. In one embodiment, the surgical tool 10 may further preferably include a lock or latch mechanism 70 for securing the relative positions of the inner and outer housings, 50 and 40, respectively, during use of the surgical tool 10. Additional features and details of the surgical tool 10 of the present embodiment will be explained with particular reference to FIGS. 6 through 8.

Figure 1:
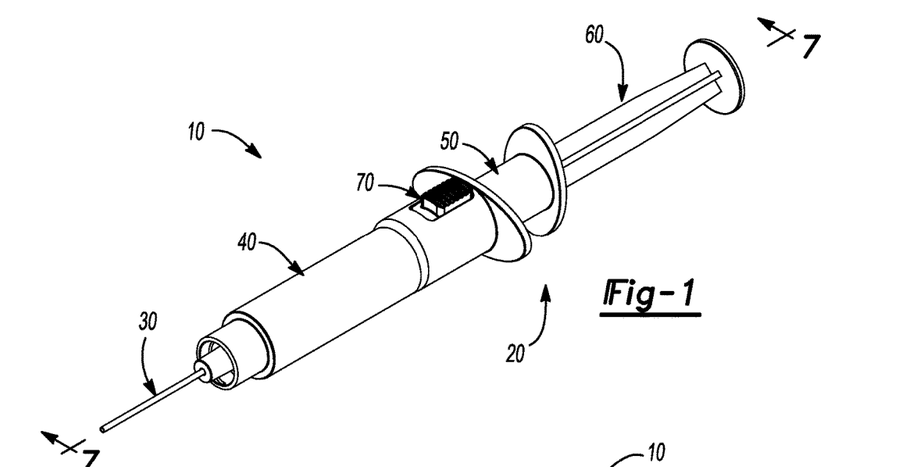
FIG. 1 is a graphic, perspective view of a surgical tool of one embodiment of the present disclosure.
Figure 2:
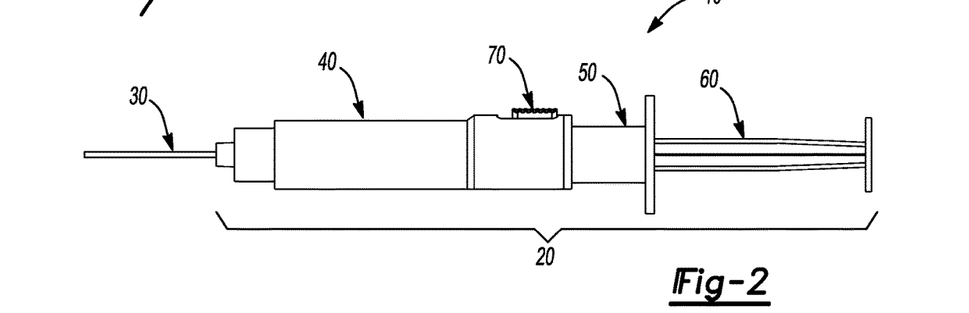
FIG. 2 is a graphic, side view of the surgical tool of FIG. 1.
Figure 3:
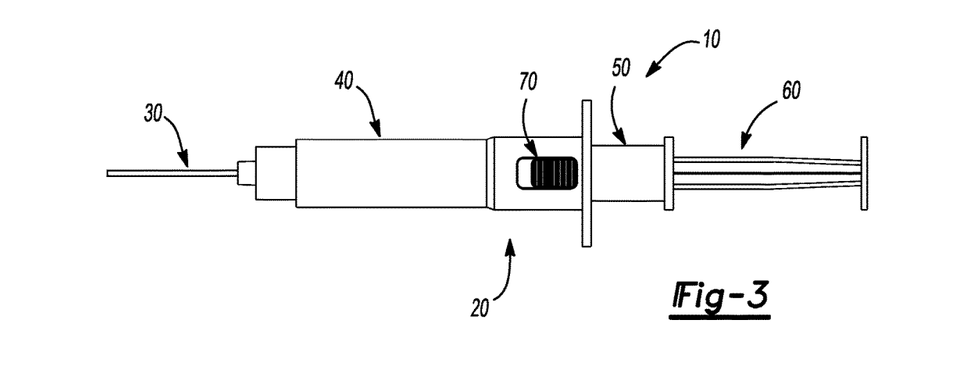
FIG. 3 is a graphic, top view of the surgical tool of FIG. 1.
Figures 4, 5, 6:
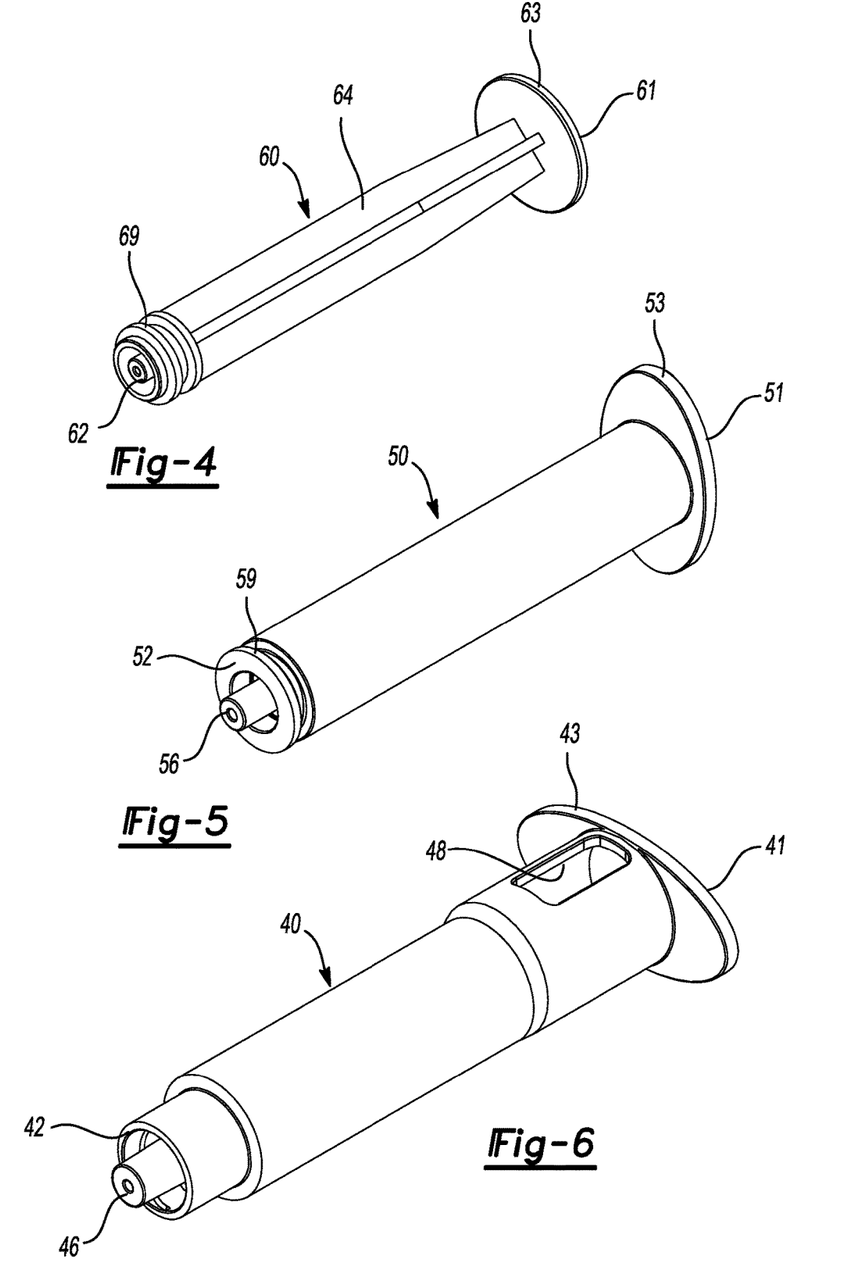
FIG. 4 is a graphic, perspective view of a plunger of the surgical tool of FIG. 1.
FIG. 5 is a graphic, perspective view of an inner housing of the surgical tool of FIG. 1.
FIG. 6 is a graphic, perspective view of an outer housing of the surgical tool of FIG. 1.

In one embodiment, as shown in FIG. 6, the first or outer housing 40 may preferably include a first or proximal end 41 and a second or distal end 42. The first or outer housing 40 may further include a generally oblong, disc-shaped, extension or shoulder 43 located proximal the first end 41. The first housing 40 may generally have a cylindrical shaped expanse and may include a passage 44 generally extending from the opening in the first end 41 and forward the generally closed bottom 45 of the passage 44 located proximal the second end 42. The generally closed bottom 45 of the passage 44 may include a shaped passage 46 extending from the bottom 45 toward the distal end 42. The passage 44 of the outer housing 40 may include an expanded or larger portion 47 located proximal the end 41 and further including a generally rectangularly shaped hole or passage 48 extending externally from the passage 44 and located proximal the extension 43.

The second or inner housing 50 may preferably include a first or proximal end 51 and a second or distal end 52. The inner housing 50 may include a generally oblong, disc-shaped, extension or shoulder 53 located proximal the first end 51. The second housing 50 may have a cylindrical shaped expanse and may include a passage 54, having a generally disc shaped cross-section, the passage 54 generally extending from an opening in the first end 51 and toward a bottom 55 of the passage 54. The bottom 55 of the passage 54 may include a centrally-located, passage 56 for receiving a portion of the basket device 30 and located in a formed, central extension 57 formed in the bottom 55. The passage 56 may include a first portion for coupling the end 35 of the sheath 32 to the housing 50 so that movement of the housing 50 directly results in movement of the sheath 32. The passage 56 may include a second portion in communication with the first portion, the second portion for allowing the wire 31 of the basket device 32 to pass through the passage 56 such that the wire 31 may move with respect to the housing 50.

The bottom 55 of the passage 54 of the housing 50 may further include radially located, plurality of passages 58 for providing a fluid communication path between the interior passage 54 of the inner housing 50 and the interior passage 44 of the outer housing 40 during operation of the surgical tool 10. In one particular embodiment, the bottom 55 of the passage 54 of the housing 50 may include first and second passages 58 located opposite each other from the central axis of the housing 50. The distal end 52 of the housing 50 may include a circumferentially located, annular notch or passage 59 for receiving a seal or O-ring 94 for sealing the inner wall of passage 44 of the outer housing 40 and the outer wall of the inner housing 50 as shown in FIG. 8. Similar to how the passage 44 of the outer housing 40 is defined by the inner wall of the outer housing 40 (which has a generally cylindrical shape), the passage 54 is defined by the inner surface (which has a generally cylindrical shape) of the second inner housing 50. Accordingly, the outer and inner housings, 40 and 50, respectively, generally make up the cylinders of the piston and cylinder mechanism 20.

Figure 7:
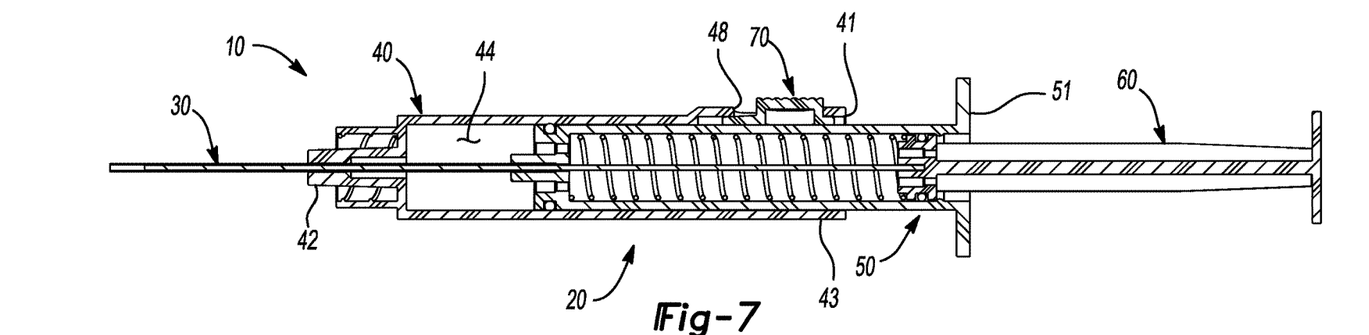
FIG. 7 is a partial, graphical side view of the surgical tool of FIG. 1.

The plunger 60 of the surgical controller tool 10 as shown in FIGS. 4, 7 and 8. The plunger 60 may generally have an overall design and construction similar to other plungers or pistons of a syringe. The plunger 60 may generally have a longitudinal extant and axis and may include a first or proximal end 61 and a second or distal end 62. The plunger 60 may further include a generally disc shaped extension or shoulder member 63 located proximal the first end 61 of the plunger 60 as shown in FIG. 4. The plunger may further include a plurality of ribs or extension members 64 extending distally from the shoulder member 63 of the first end 61 and to a piston member 65 located proximal the second end 62 of the plunger 60.

The piston member 65 may generally have an overall, disc or cylinder shaped body including a centrally located axial passage 66 extending from the second end 62 and toward the first end 61 for securely receiving the first end 36 of the wire 31. The first end 36 of the wire 31 may be coupled to the passage 66 using any known or appropriate fastener, coupler, or other design for coupling a wire to a passage. The first end 36 of the wire 31 may be securely coupled to the end 62 of the plunger 60 so that any movement of the plunger 60 will directly result in movement of the wire 31, as shown in FIG. 8. The piston member 65 may further include a first, annular shaped shoulder 67 located proximal the second end 62. The piston member 65 of the plunger 60 may further include an annular notch or passage 69 as shown in FIGS. 4 and 8 for receiving an O-ring or seal 90 as shown in FIG. 8.

Similar to the passages 58 in the second, inner housing 50, the piston member 65 of the plunger 60 may include a plurality of passages 68 extending from the second end 62 and through the piston member 65 for communicating fluid between the interior passage 54 of the second housing 50 and the atmosphere external the surgical tool 10. In the current embodiment, the plunger 60 of the surgical tool 10 may include four passages 68 wherein each passage 68 may be located between two ribs 64 of the plunger 60. In this embodiment, each passage 68 may be located radially distal the central axis of the plunger and angularly offset by approximately 90° from two of the other passages 68. The passages 68 may also be located at other radial and angular locations in the piston member 65. Considering the above description regarding the first outer housing 40, it may be appreciated that the fluid in the internal passage 44 of the housing 40 may move through the passages 58 in the bottom 55 of the inner housing 50 and the passages 68 in the piston 65 during operation of the surgical tool 10. Similarly, in reverse order, fluid in the atmosphere of the surgical tool 10 may move through the passages 68 in the piston 65 of the plunger 60 into the internal passage 54 of the second housing 50 and then through the passages 58 in the bottom 52 of the second housing 50 into the internal passage 44 of the first housing 40 during operation of the surgical tool 10.

The surgical controller tool 10 may further include a biasing mechanism or first spring 80 located in the internal passage 54 of the second or outer housing 50 in the current embodiment. The biasing mechanism 80 may preferably be a coil spring 80. The biasing mechanism 80 may preferably be a compression coil or helical spring, by way of example, made of an elastic material and formed into the shape of a helix and having a natural unloaded length greater than the length of the internal passage 54. More particularly, the coil spring 80 may include a first or proximal end 81 circumscribing at least a portion of the end shoulder 67 of the end of the piston member 65 of the plunger 60. The coil spring 80 may include a second or distal end 82 for engaging the bottom 55 of the second housing 50. Since the coil spring 80 is in compression when located in the internal passage 54, the coil spring 80 biases or forces the plunger 60 and the housing 50 in opposite directions which causes the end 36 of the wire 31 to move in a direction opposite of the end 35 of the sheath 32 thereby biasing the basket device 30 toward a first or closed position wherein the end 38 of the wire 31 is within the sheath 32 and there is no basket 33 present in the first or closed position. Whether the spring 80 biases the first or outer housing 40 will depend upon whether the latch 70 is locked or unlocked. When the latch 70 is locked and the first and second housings 40 and 50, respectively, are coupled, the biasing force of the spring 80 will be transferred to the outer housing 40. When the latch 70 is unlocked, the biasing force of the spring 80 will not be transferred to the outer housing 40.

In one embodiment, the internal passage 54 of the housing 50 may preferably include a inwardly projecting extension, shoulder or bump portion 54a located proximal the first end 51 and further defining the internal passage 54, as shown in FIG. 8. The extension portion 54a may preferably provide a narrower passage portion than the outer diameter of the piston end 65 of the plunger 60 such that the piston end 65 of the plunger 60 may be retained within passage 54 of the housing 50 despite the force of the spring 80 biasing the plunger 60 in an longitudinal, axial direction out of the passage 54 but only to the point where the piston 65 of the plunger contacts the inwardly projecting member 54a of the passage 54 and the plunger 60 is prevented from being moved further away from the bottom 55 and from being removed or ejected from the first end 51 of the second housing 50 as shown in FIG. 8.

The surgical tool 10 may further include a latch or lock assembly 70 for selectively securing the relative positions of the first and second housings 40 and 50, respectively, as well as thereby controlling and selectively securing the respective positions of the end 36 of the wire 31 with respect to the end 35 of the sheath 32. The latch 70 may include a button 71 including an upper surface 72 for being engaged by a finger or thumb of an operator of the surgical tool 10. The upper surface 72 may be roughened or knurled for more positive engagement by the operator. The button 71 may include a first surface 73 and a second surface 74 aligned substantially perpendicular to the upper surface 72 for providing abutments with the edges of the passage 48 of the first housing 40 when the button 71 is moved between an unlocked position (as shown in FIGS. 7 and 8) and a locked position. The button 71 may further include a first lower extension member 75 extending substantially perpendicular to the first end surface 73 and substantially parallel with the upper surface 72 and having a portion contacting the outer surface of the second housing 50. The button 71 may further include a second lower extension member 76 extending substantially perpendicular to the second end surface 74 and aligned substantially parallel with the upper surface 72 and having a bottom portion contacting the outer surface of the second housing 50. The first and second lower extension members 75 and 76, respectively, extend beyond the opening 48 in the housing 40 to prevent the button 71 from being removed from the passage 48. An upper surface 77 of the second lower extension member 76 may preferably include a cam angle for engaging the expanded interior surface portion 47 of the passage 44 of the first housing 40. The upper surface 77 may preferably include a cam angle and design such that when the button 71 is in the unlocked position of FIG. 8, the latch 70 does not prevent relative movement of the first and second housings 40 and 50, respectively. When the button 71 is moved away from the open or unlatched position and toward the latch or locked position, the upper cam surface 77 engages the interior surface of the expanded portion 47 of passage 44 and generates a locking force to prevent relative movement of the first and second housings 40 and 50, respectively.

The surgical controller tool 10 may further include a portion of a luer fitting 84 for coupling the surgical controller tool 10 to a y-port of an endoscope (not shown). It will be appreciated that while a male luer fitting 84 is shown, alternatively a female luer fitting 84 for coupling the surgical tool 10 to an endoscope having a male luer fitting. It will be appreciated that other types of fittings, adapters sealing threads, manifolds and fittings may alternatively be used for coupling the surgical tool 10 to the y-port or endoscope or other surgical apparatus (not shown).

The surgical controller tool 10 may be used to open and close the basket 33 of the basket device 30 by moving the plunger 60 axially in the housing 50 against the biasing force of the spring 80 such that there is relative movement of the wire 31 with respect to the sheath 32 from the closed position and toward the open position. This may be accomplished single-handedly by an operator gripping the extension member 53 of the housing 50 between, preferably, the index and middle fingers and then placing a thumb on the extension member 63 or end 61 of the plunger 60. In use, the operator increases the amount of force the thumb places on the end 61 of the plunger 60 until the pressing force of the operator's thumb is greater than the biasing force of the spring 80 (and any internal forces associated with the piston 65 and the seal 90) and the piston 65 begins to move from the closed basket device 30 position and along the longitudinal axis of the surgical tool 10 and toward the end 52. As the piston 65 moves in the internal passage 54, the wire 31 is moved with respect to the sheath 32 and the end 38 of the wire 31 extends beyond the end of 37 of the sheath 32 to allow the wire 31 to open into the basket 33. Once the operator moves the basket 33 to surround the object to be removed from the body, the operator may reduce the amount of some force on the end 61 of the plunger below the biasing force of the spring 80 so the piston 65 moves toward the end 51 of the housing 50. Before, during and or after movement of the piston 35 within the interior passage 54, the operator of the surgical controller tool 10 may selectively operate the latch 70 to unlatch the first and second housings 40 and 50, respectively, and to move the housing 50 and the sheath 32 with respect to the housing 40 which is connected to the Y-port of the endoscope. The ability to move the housing 50 selectively and controllably in the housing 40 provides the operator with greater control of the basket 33 of the basket device 30 during the object removal procedure. Once the operator moves the housing 50 to a desired position within the housing 40 to locate the end 38 of the wire 31 and/or the basket 33, the button 71 of the latch 70 may be moved in the passage 48 of the housing 40 so that the camping surface 77 engages the expanded interior surface 47 of the passage 44 to generate sufficient force there between two secure the position of the housing 50 within the housing 40. Before, during, or after this action, it is possible for the operator to selectively move the piston 65 within the housing 50 for controlling the opening and closing of the basket 33 during the procedure to remove the object from the body.

During operation of the piston and cylinder mechanism 20 of the surgical tool 10, it may be appreciated that the operator may accomplish the opening and closing of the basket device 30 using only one hand. Accordingly, the surgical controller tool 10 allows the surgeon to control other surgical devices while using the device of the present design. This may make it possible for the operator to perform the object removal procedure without the involvement of an attendant. The above may reduce the possibility of unintended movements of the basket device 30 resulting in loss of objects or portions thereof during the object capture procedure thereby delaying removal of the object from the body. The surgical controller device 10 of the present disclosure may be used for other procedures and with other devices.

Figure 9:
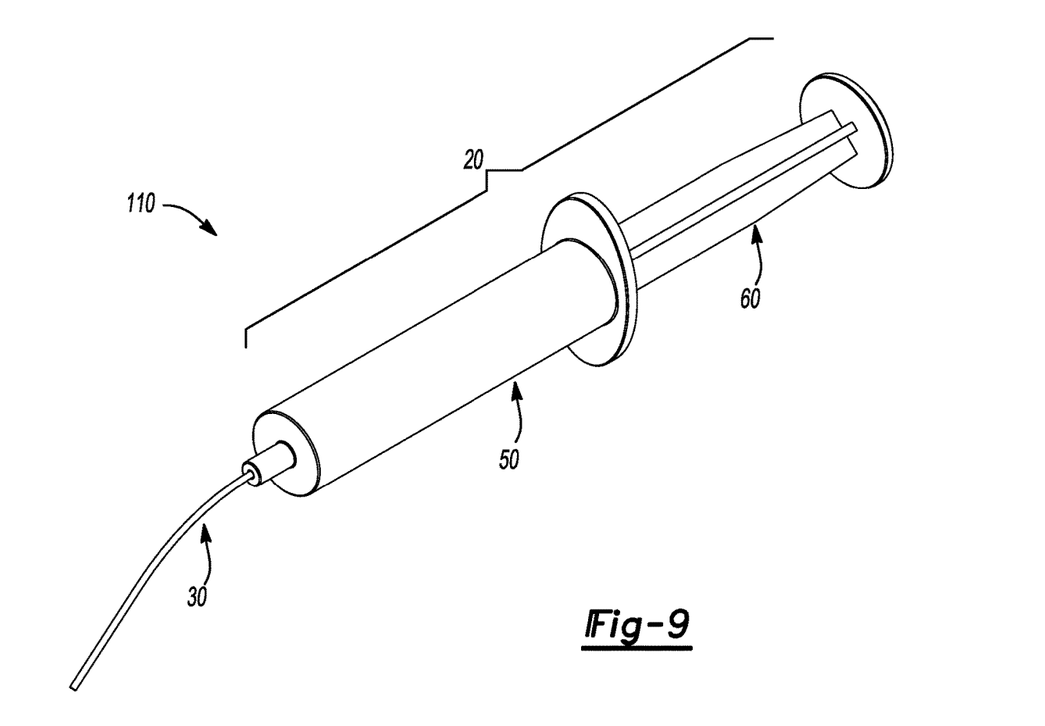
FIG. 9 is a graphic, perspective view of a surgical tool of one embodiment of the present disclosure.
Figure 10:
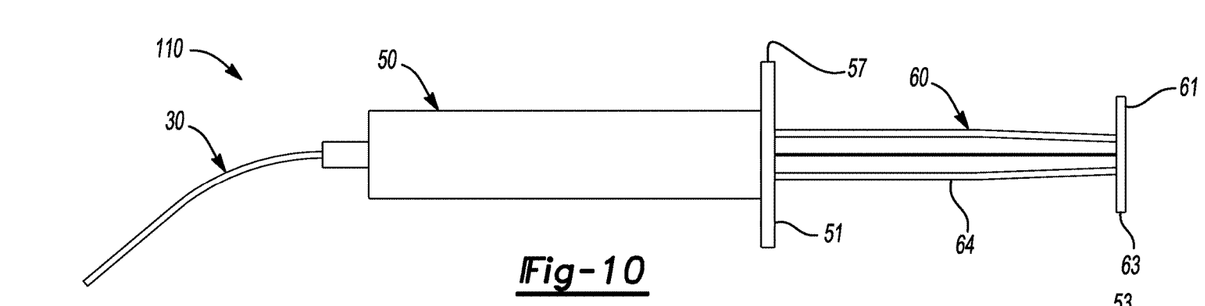
FIG. 10 is graphic, side view of the surgical tool of FIG. 9.
Figure 11:
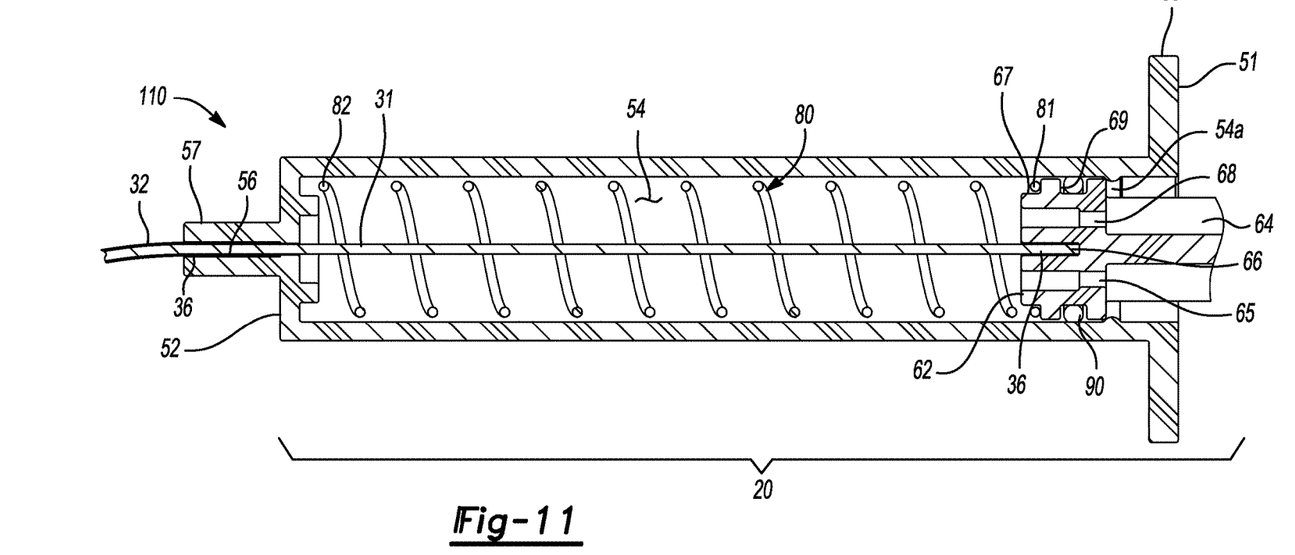
FIG. 11 is a partial, graphical side view of the surgical tool of FIG. 9.
Figure 12:
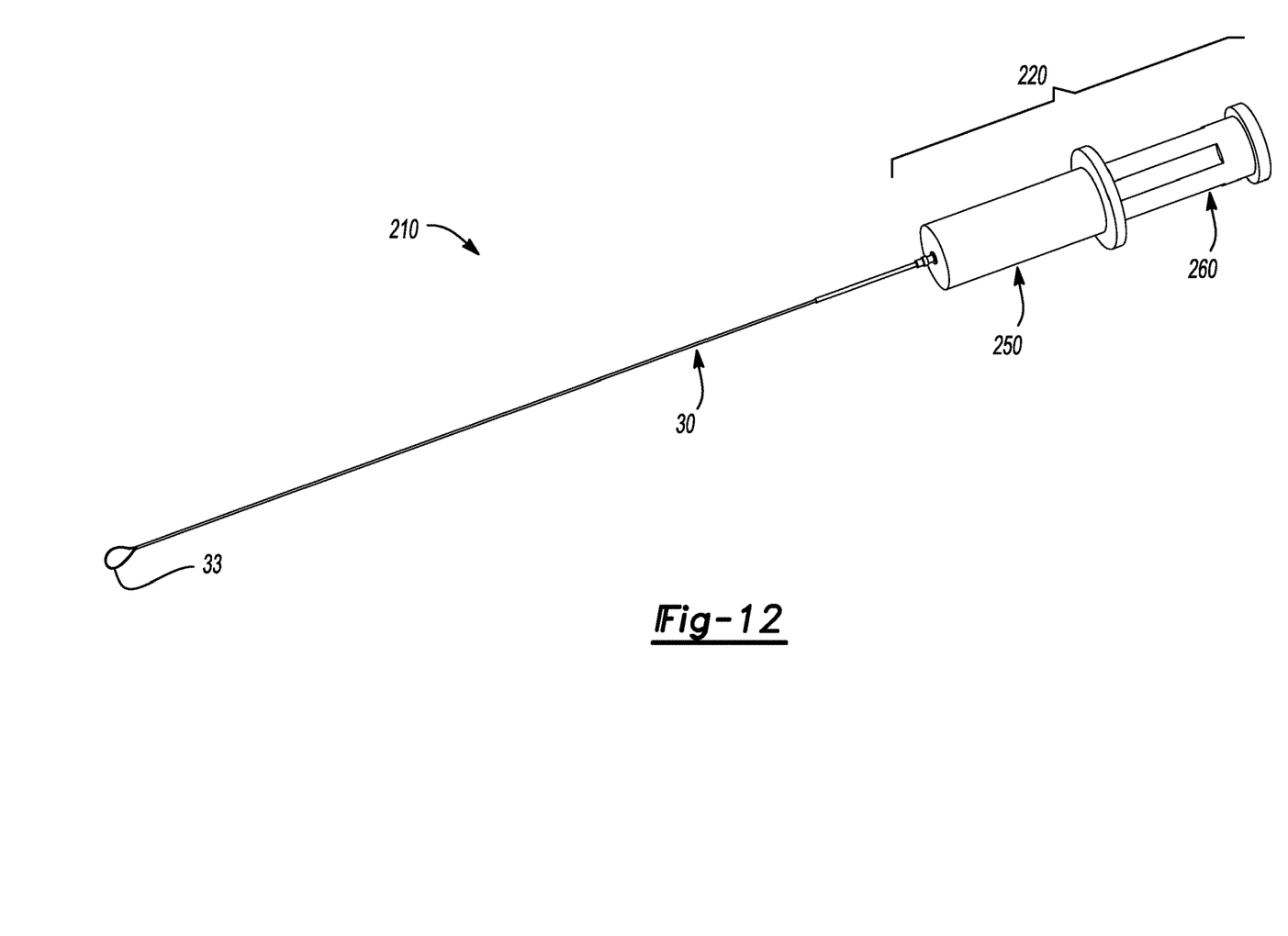
FIG. 12 is a graphic, perspective view of a surgical tool of one embodiment of the present disclosure.
Figures 13, 14:
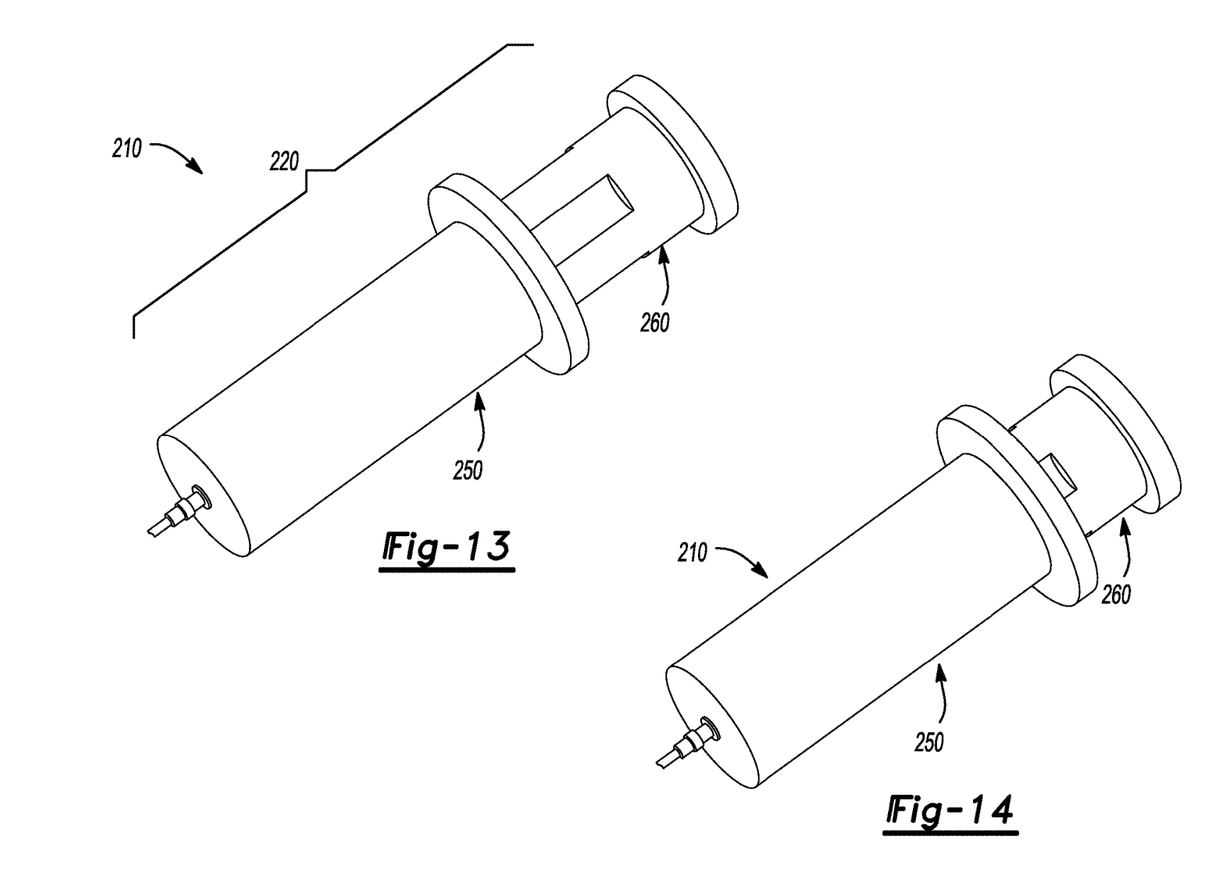
FIG. 13 is an alternate, graphic, perspective view of the surgical tool of FIG. 12 in a first position.
FIG. 14 is an alternate, graphic, perspective view of the surgical tool of FIG. 12 in a second position.

Referring now to the embodiment of FIGS. 9 through 11, there is disclosed a surgical controller tool 110 which is a simplified version of the surgical controller tool 10. In particular, it may be appreciated that the surgical controller tool 110 does not include first and second housings but instead only includes the housing 50. Since the housing 50 is not received in another housing, the structures associated with that connection are no longer present in the surgical controller tool 110. Additionally, the surgical controller tool 110 may include the housing 50, the plunger 60 and the basket device 30 all of which are substantially similar, if not identical, to their respective counterparts in the surgical tool 10 of the prior embodiment. The housing 50 of the surgical tool 110 may include a first end 51 and a second end 52. The second end 52 no longer includes a seal 90 between the exterior of the housing 50 and the interior of the housing 40 since the surgical tool 110 does not include a housing 40. The housing 50 of the surgical tool 110 may include a passage 56 in the end 52 for receiving the end 35 of the sheath 32 of the basket device 30. The wire 31 passes through the passage 56 in the second end 52 of the housing 50, including passing through the reduced shaped portion of the passage 56, and extends through the interior passage 54 of the housing 50 where the end 36 of the wire 31 is coupled to a passage 66 in the end 62 of the syringe 60.

The surgical tool 110 may be used to open and close the basket 33 of the basket device 30 by moving the plunger 60 axially in the housing 50 against the biasing force of the spring 80. This may be accomplished single-handedly by an operator (i.e., generally a surgeon) gripping the extension member 53 of the housing 50 between, preferably, the index and middle fingers and then placing a thumb on the extension member 63 of the plunger 60. In use, the operator increases the amount of force the thumb places on the end 61 of the plunger 60 until the pressing force of the operator's thumb is greater than the biasing force of the spring 80 (and any internal forces associated with the piston 65 and the seal 90) and the piston 65 begins to move from the closed basket device 30 position and along the longitudinal axis of the surgical tool 110 and toward the end 52. As the piston 65 moves in the internal passage 54, the wire 31 is moved with respect to the sheath 32 and the end 38 of the wire 31 extends beyond the end 37 of the sheath 32, shown in FIG. 21, to allow the wire 31 to open into the basket 33. Once the operator moves the basket 33 to surround the object to be removed from the body, the operator may reduce the amount of some force on the end 61 of the plunger below the biasing force of the spring 80 so the piston 65 moves toward the end 51 of the housing 50. Again, it may be appreciated that the surgical controller tool 110 may be operated single-handedly by a surgeon for removing an object from a body or other procedures.

Figure 15:
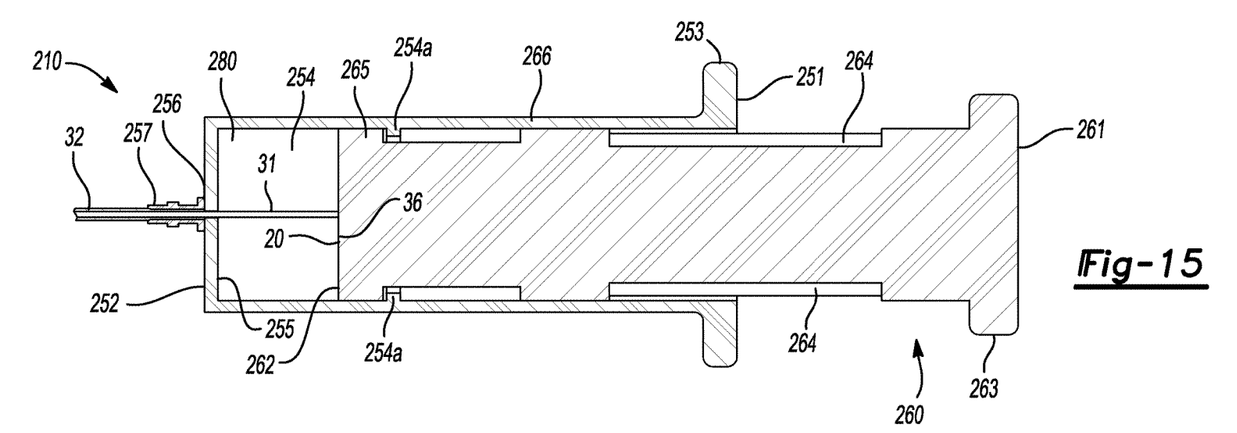
FIG. 15 is a partial, side section view of the surgical tool of FIG. 13.
Figure 16:
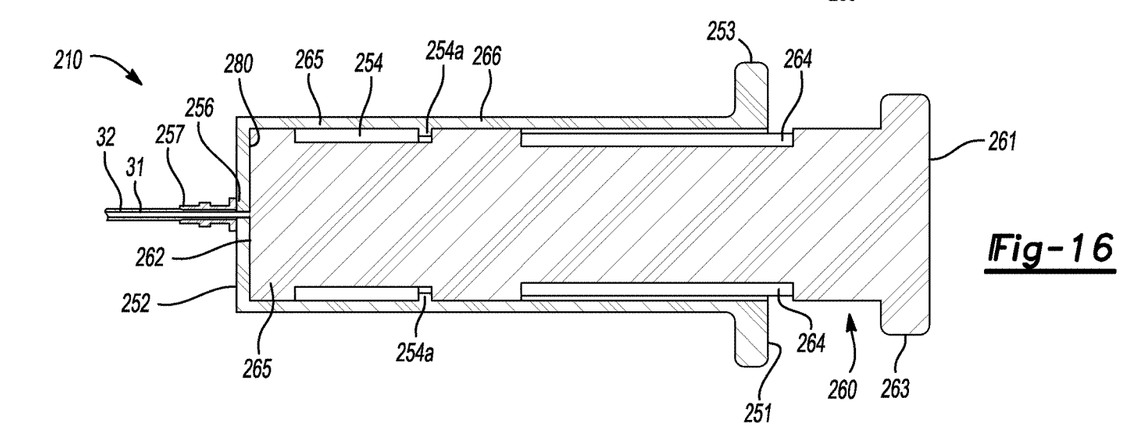
FIG. 16 is a partial, side section view of the surgical tool of FIG. 14.

Referring now to the surgical controller tool 210 of FIGS. 12 through 18, an alternate piston and syringe 220 configuration may include a housing 250 and a plunger 260 for controlling the basket device 30 for opening and closing the basket 33 by relative movement of the wire 31 and the sheath 32. The housing 250 is a generally cylindrical shaped design, similar to the housing 50, and may include a first or proximal end 251 and a second or distal end 252. The first end 252 of the housing 250 may include a shoulder or extension member 253 similar to that of the housing 50. The housing 250 may further include an interior passage 254 defined by an inner wall of the housing 250. In the surgical tool to 10, the passage 254 of the housing 250 may further include an inwardly extending shoulder or extension member 254a located between the first end 251 and the second end 252. Particularly, the extension member 254a may be located more proximal to the end 252 than to the end 251 for engagement with a piston 265 of the plunger 260 as shown in FIGS. 15 and 16. Additionally, the plunger 260 may include the piston 265 located proximal the end 252 and an intermediary piston 266 for defining a narrowed piston portion 267 for defining a length of travel of the plunger 260 in the interior passage 254 of the housing 250 based upon the relative position of the extension member 254a between the opposing walls of the piston 265 and the intermediary piston 266. In this embodiment, the ribs or extension members 264 of the plunger 260 do not extend along the narrowed piston portion 267.

The first or proximal end 36 of the wire 31 may be securely coupled to the end 262 of the plunger 260 using any known or appropriate coupling, fastening or securing devices, mechanisms and/or arrangements. The second end 252 of the housing 250 may include a central passage 256 through which the wire 31 passes. The first or proximal end 35 of the sheath 32 may be coupled to the end 252 of the housing 250 using an extension member 257. Accordingly, it may be appreciated that the sheath 32 is anchored with respect to the housing 250 and the wire is anchored with respect to the plunger 260.

The biasing mechanism 280 may be a compression spring 280 similar to the above embodiment for the spring 80 and, alternatively, may be a biasing mechanism including an elastic or other material located between the end 262 of the plunger 260 and the bottom 255 of the interior passage 254 of the housing 250. The biasing mechanism 280 moves the plunger 260 axially along the longitudinal axis of the surgical controller tool 210 to move the wire 31 with respect to the sheath 32 for opening and closing the basket 33 of the basket device 30. Again, it may be appreciated that an operator of the surgical controller tool 210 may single-handedly operate and control the opening and closing of the basket 33 of the basket device 30. For the surgical controller tool 210, the operator may place the housing 250 in the palm of her hand with the extension member 253 side of the palm proximal the thumb and then wrap her fingers around the outer surface of the housing 250 and then place the thumb on the end 261 of the plunger 260. Additionally, for the surgical controller tool 210, the operator may place the housing 250 between the index and middle fingers which may wrap the extension member 253 of the end 251 and then place her thumb on the end 261 of the plunger 260. In either arrangement, the operator may use thumb force to single-handedly move the plunger 260 in the interior passage 254 of the housing 250 to move the wire 31 with respect to the sheath 32 for operating the basket device 30 between a closed position (FIGS. 12, 13 and 15) and an opened position (FIGS. 14 and 16) where the basket 33 may be located proximal the object to be removed from the body and then the basket 33 controllably moved toward the closed position to capture the object.

Figure 19:
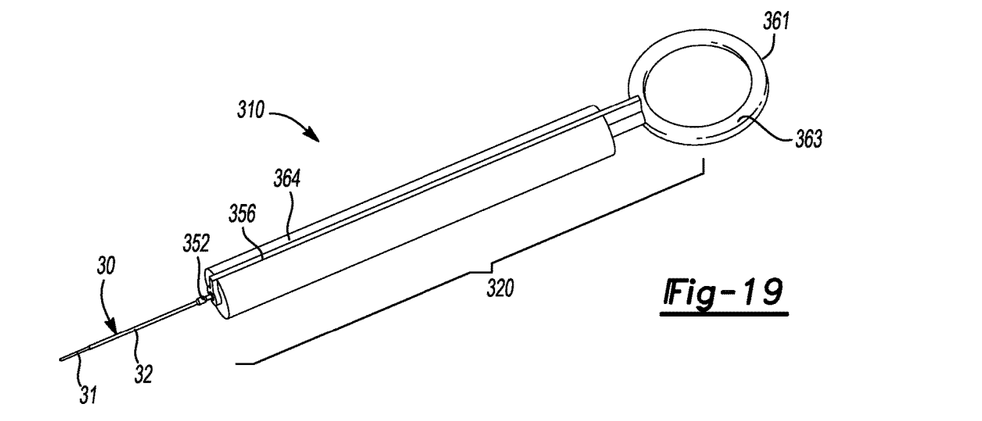
FIG. 19 is an alternate, graphic, perspective view of the surgical tool of FIG. 17 in a second position.
Figure 20:
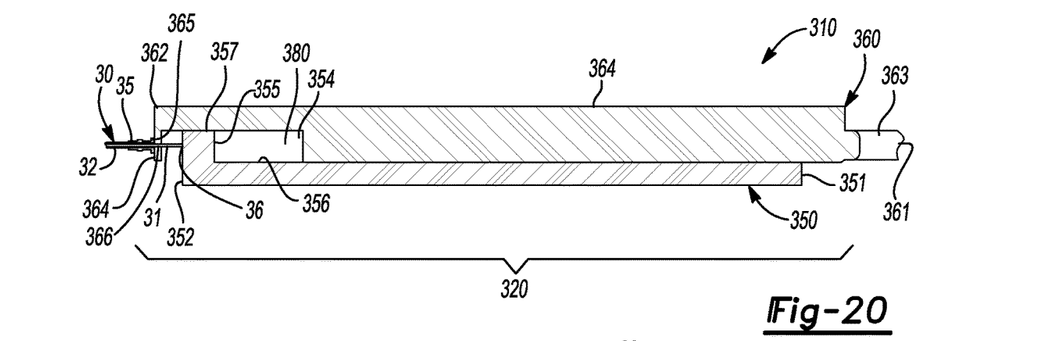
FIG. 20 is a partial, side view of the surgical tool of FIG. 19.

Referring now in particular to FIGS. 17 through 20 there is shown a surgical controller tool 310 according to the present disclosure. While different from the surgical controller tools 10, 110 and 210, the surgical controller tool 310 may still generally include a piston and cylinder arrangement 320. In particular, the surgical controller tool 310 may be used with any known or appropriate basket device 30 including a wire 31 and a sheath 32, wherein the relative movement of the wire 31 with respect to the sheath 32 may form a basket 33 for use in capturing an object to be removed from a body. The surgical controller tool 310 is simplified and efficient and may include a housing or handle 350 having a generally round or cylindrical construction as best shown in FIGS. 19 and 20. The housing or handle 350 may generally have a longitudinal extant defining a longitudinal axis and may include a first end 351 and a second or opposite end 352. The housing 350 may further include a passage 354 extending longitudinally from the first end 351 and toward the second end 352 to a bottom or wall 355 of the passage 354 located proximal the second end 352 as shown in FIG. 20. The passage 354 may have a substantially, rectangularly-shaped cross-section extending generally, radially from a bottom wall 356 and substantially perpendicular to the longitudinal axis of the housing handle 350. Referring in particular to FIG. 20, the passage 354 may extend to the outer periphery or surface of the housing handle 350. The housing handle 350 may include a reduced end wall portion 357 extending from the end 352 and to the interior wall 355. The surface of the end wall portion 357 may be aligned substantially parallel and offset with the bottom wall 356 for supporting the movement of the plunger 360 within the housing handle 350.

The surgical controller tool 310 may include a plunger actuator 360 having a generally longitudinal extending body 364 generally extending between a first end 361 and a second end 362. The first entry 61 of the plunger actuator 360 may include a ring 363 for engagement by an operator for moving the plunger actuator 360 with respect to the housing handle 350. The body 364 may generally be shaped complimentary any of the cross-section shape of the passage 354 for longitudinal axial movement with respect thereto. The plunger actuator 360 may further include a wall or extension member depending perpendicularly from the body 364 proximal the second end 362 and including a passage 366 for having the wire 31 pass there through and for the end 36 of the wire 31 to be coupled to the end 352 of the housing 350. The end 35 of the sheath 32 may be coupled to the plunger actuator 360 proximal the end 362 and externally of the passage 366. Accordingly, the wall 365 of the plunger actuator 360 may be located proximal the second end 352 of the housing handle 350 and aligned substantially perpendicular to the longitudinal axis of the plunger actuator 360 and the longitudinal axis of the housing handle 350.

The surgical controller tool 310 may further include a biasing mechanism 380 located in the passage 354 between the wall 355 and the body 364 for generating a biasing force to move the surgical controller tool 310 and the basket device 30 toward the closed position as best shown in FIGS. 17, 18 and 20. Upon application of sufficient force by the operator to overcome the biasing force of the biasing mechanism 380, the plunger actuator 360 may be moved longitudinally axially with respect to the housing handle 350 and the wire 31 may be moved with respect to the sheath 32 to extend the end 38 of the wire from the end 37 of the sheath to open the basket 33 as shown in FIGS. 19 and 21.

Figure 22:
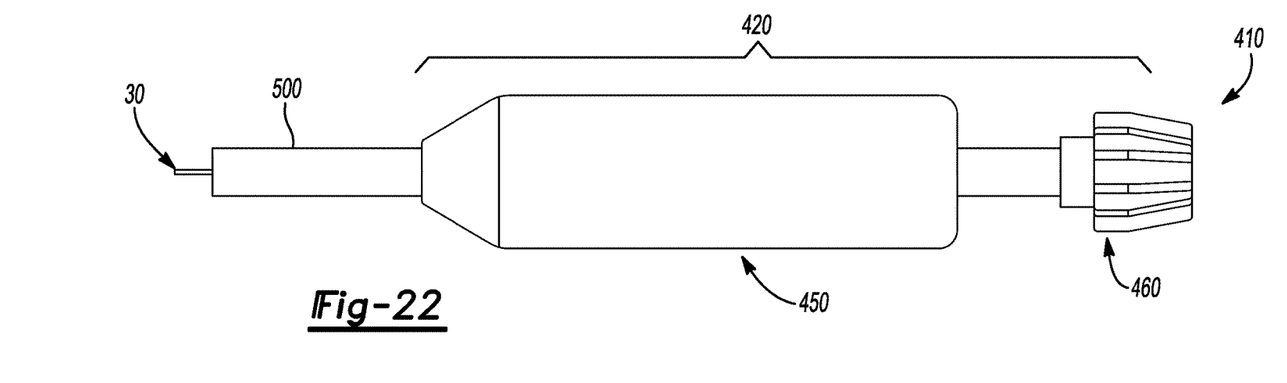
FIG. 22 is a side, graphic view of a surgical tool according to one embodiment of the present disclosure.
Figure 23:
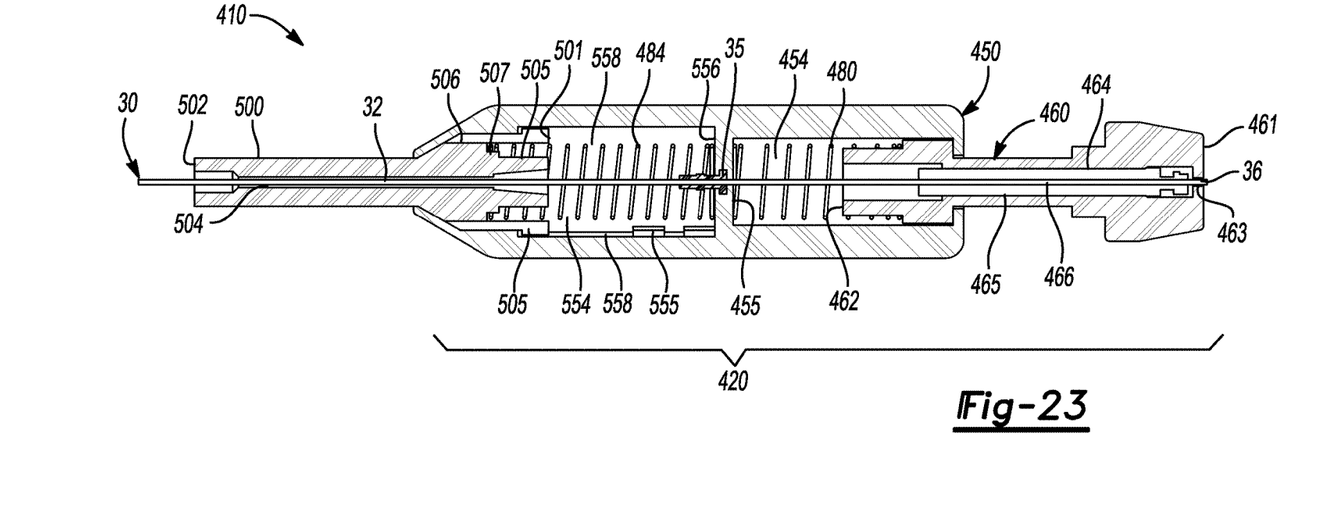
FIG. 23 is a side, partial graphic view of the surgical tool of FIG. 22.

Referring now in particular to FIGS. 22 and 23, a surgical controller tool or handle 410 may include a basket device 30, a piston plunger mechanism 420, a housing handle 450 and a plunger 460 according to one embodiment of the present disclosure. The surgical controller 410 is a double spring embodiment and may include a rigid connector 500 for coupling the surgical controller 410 to an endoscope (not shown). Referring in particular to FIG. 23, the housing handle 450 of the surgical tool 410 may have a generally overall cylindrical shape for one-handed operation by an operator. The double spring surgical tool 410 has particular application in use with a basket device 30 and an endoscope wherein the surgical tool 410 may control the retraction of the sheath 32 of the basket device 30 relative to the endoscope (not shown). The rigid connector 500 of the surgical tool 410 may include a first end 501 and a second end 502 further defined by an internal central axis aligned passage 504 extending between the first and second ends 501 and 502, respectively. The sheath 32 and wire 31 of the basket device 30 extend through the passage 504 of the rigid connector 500 for coupling with respect to the housing handle 450 and the plunger actuator 460, respectively.

The rigid connector 500 may further include a generally conical shaped portion 506 located proximal the end 501 and including a plurality of outwardly projecting extension tabs 505 as shown in FIG. 23. The portion 506 may be located in a passage 554 of the housing handle 450. The rigid connector 500 of the surgical tool 410 may further include an annular passage portion located proximal the end 501 and extending toward the portion 506 proximal the collar supporting the extension tabs 505 for receiving an end of a second biasing member 484 for biasing the rigid connector 500 away from the plunger actuator 460 and in a direction actually toward the endoscope (not shown). The passage 554 of the housing handle 450 may include notches or landings 555 for receiving the extension tabs 505 of the collar 506 when the rigid connector 500 is moved toward the end 556 of the passage 554 against the biasing force of the second biasing member 484. The passage 554 of the housing handle 450 may further be defined by a plurality of extension passages 558 for receiving the extension tabs 505 when the rigid connector 500 is biased in an axial direction away from the plunger actuator 460 and the extension tabs 505 are free from the notches 555 and the biasing force of the biasing mechanism 484 moves the rigid connector 500 and the portion 506 away from the plunger actuator 460.

The housing handle 450 may further include an internal passage 454 including an end 455 for receiving and anchoring the end 35 of the sheath 32, with respect to the housing handle 450. The surgical tool 410 may further include the first biasing mechanism or compression spring 454 for biasing the plunger actuator 460 in a direction away from the end 455 of the passage 464 as shown in FIG. 23. The plunger actuator 460 may include a first end 461 and a second end 462 and a centrally located passage 464 extending there between. The plunger actuator 460 may further include an insert 465, including a centrally aligned passage 466 for being received in the passage 464 thereof and for receiving the wire 31, the end 36 of which is non-rotatably, anchored in a hole or passage 463 in the end 461 of the plunger actuator 460.

It may be appreciated that the plunger actuator 460 of the surgical tool 410 may be moved against the biasing force of the biasing member 484 to move the wire 31 with respect to the sheath 32 for actuating the basket device 30. Additionally, with the rigid connector 500 coupled to an endoscope, the handle 450 of the surgical tool 410 may be moved against the biasing force of the second biasing member 484 so that the tabs 505 may be moved along the slots 558 and toward the notches 555 to move the sheath 32, with respect to the endoscope. Once the tabs 505 are located proximal the notches 555, the housing handle 450 may be rotated to locate the tabs 505 in the notches 555 and thereby secure the location of the rigid connector 500 within the passage 554 against the biasing force of the biasing member 484. In this position, the plunger actuator 460 may still be separately and selectively operated to move the wire 31 with respect to the sheath 32 to open and close the basket 33 for capturing the object to be removed from the body.

Applicants hereby assert that the present disclosure is intended to be illustrative and not restrictive as will be understood by a person having ordinary skill in the art. Many embodiments as well as many applications besides the examples expressly disclosed and taught herein will become apparent to those of ordinary skill in the art upon understanding the present disclosure. The scope of the claimed invention shall not be determined with limiting reference to the present disclosure unless expressly intended by applicants, and should instead be determined with reference to the appended claims, along with the full scope of equivalents to which such claims are entitled. Any disclosure of an article or reference, including patent applications and publications, is intended to be an incorporation by reference herein for all purposes. Any omission in the following claims of any aspect of subject matter disclosed herein is not a disclaimer of such subject matter.

For purposes of clarity, the applicant hereby notes that any numerical values recited herein or in the figures are intended to include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, then it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. Also for purposes of clarity, the applicants in tend that the teaching of amounts expressed as "parts by weight" herein also contemplates the same ranges expressed in terms of percent by weight unless otherwise stated or logical. Thus, an expression herein that a range in terms of at least "x parts by weight of a polymeric blend composition" also contemplates a teaching of ranges of the same recited amount of "x" in percent by weight of the resulting polymeric blend composition. Unless expressly stated, all ranges are intended to include both endpoints and all numbers between the endpoints. The use of "about", "generally" or "approximately" (or similar terms) in connection with a range is intended to apply to both ends of the range. Thus, "about 20 to 30" is intended to specifically disclose and teach "about 20 to about 30", inclusive of at least the specified endpoints.

The use of the term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

The disclosure of "a" or "one" to describe an element, ingredient, component or step is not intended to foreclose additional elements, ingredients, components or steps. Plural elements, ingredients, components or steps may be provided by a single integrated element, ingredient, component or step. Alternatively, a single integrated element, ingredient, component or step might be divided into separate plural elements, ingredients, components or steps.

We claim:

1. A tool for use by a surgeon for operating a basket device for capturing an object to be removed from a body of an animal, the tool comprising:
a controller adapted to be coupled to the basket device for selectively controlling the basket device and moving it between a first, closed position and a second, open position, the controller comprising:
a piston and cylinder mechanism;
a sheath having a first end and a second end, the sheath adapted to receive the basket device and to have the basket device longitudinally slide with respect thereto between the first, closed position and the second, open position;
wherein a piston of the piston and cylinder mechanism is adapted to be coupled to one of the basket device and the sheath and a cylinder of the piston and cylinder mechanism is adapted to be coupled to the other of the basket device and the sheath and wherein the piston and the cylinder of the piston and cylinder mechanism may each be independently operated to separately actuate the basket device and the sheath;
wherein a proximal end of the sheath is received at a passage at an end of the cylinder;
a handle coupled to the cylinder;
a plunger coupled to the piston for sealingly engaging an inner wall of the cylinder; and
wherein the controller is configured to longitudinally move the sheath and the basket device with respect to each other to selectively operate opening and closing of the basket.

2. The tool of claim 1 further comprising a first biasing mechanism configured to bias the basket device toward the first, closed position with respect to the handle and the sheath.

3. The tool of claim 2 further comprising a second biasing mechanism configured to bias the basket device toward the first, closed position with respect to the handle and the sheath and further comprising a basket actuator configured to be coupled to the basket device to move the basket device toward the second, open position independent of the handle.

4. The tool of claim 3 wherein the basket device is configured to be rigidly rotationally coupled to the basket actuator.

5. The tool of claim 2 further comprising:
a second biasing mechanism configured to bias the basket device toward the first, closed position with respect to the handle and the sheath; and
wherein the basket device is configured to be rigidly rotationally coupled to the basket actuator.

6. The tool of claim 5 further comprising a luer coupler for selectively coupling the tool to an endoscope.

7. A tool for use in capturing an object inside a body of an animal, the tool comprising:
an expansible wire device including a wire and a sheath operable between a closed position and an open position, wherein an end of the wire defines a basket portion for capturing the object;
a controller comprising:
a plunger actuator having a first end and a second end, the second end directly coupled to the sheath of the expansible wire device, the plunger actuator configured to control the expansible wire device between the closed position and the open position;
a handle coupled to the plunger actuator for supporting relative movement of the plunger actuator and the handle, the handle including a first end and a second end and wherein the wire is coupled to the second end of the handle;
a biasing mechanism located between the handle and the plunger actuator configured to bias the plunger actuator toward the closed position; and wherein the sheath and the expansible wire device are adapted to longitudinally slide with respect to each other.

8. The tool of claim 7 wherein the plunger actuator has a generally elongate shape defining the first end, the second end and a longitudinal axis and having a shaped cross section having a generally linear portion and wherein the handle comprises a generally elongate body defining a first end, a second end a longitudinal axis, the handle body including a passage extending longitudinally from the first end to the second end, the passage extending radially and for receiving at least a portion of the shaped cross section of the plunger actuator therein and for supporting the relative movement of the plunger actuator and the handle.

9. The tool of claim 8 wherein the first end of the plunger actuator extends distally from the first end of the passage of the handle body and includes a ring member.

10. The tool of claim 9 wherein the plunger actuator further includes a wall portion located proximal the second end and aligned substantially perpendicularly to the longitudinal axis of the plunger actuator; and wherein the handle body includes a wall portion located proximal the second end of the handle body and further defining the passage of the handle body, the wall portion of the handle body and the wall portion of the plunger actuator abutting when the tool is in the open position.

11. The tool of claim 8 wherein the handle and the plunger actuator comprise a syringe wherein the handle includes a tube including a passage which receives the plunger actuator which is moveable between the open position wherein the second end of the plunger actuator is located proximal the second end of the tube and the closed position wherein the second end of the plunger actuator is located distal from the second end of the tube.

12. The tool of claim 11 wherein the passage of the tube of the handle includes an intermediate wall located between the first and second ends of the tube and wherein the plunger actuator includes a shoulder portion located proximal the second end of the plunger actuator and wherein the movement of the shoulder portion of the plunger actuator is restrained between the second end of the tube and the intermediate wall of the tube.

13. The tool of claim 7 further comprising a y-port connector for coupling the tool to an endoscope.

14. The tool of claim 7 wherein the tool is slidably connected to an endoscope working channel.

15. The tool of claim 7 further comprising a lock for selectively locking the plunger actuator and the handle for preventing relative movement of the plunger actuator and the handle.

* * * * *